(12) United States Patent
Sato et al.

(10) Patent No.: US 6,645,735 B2
(45) Date of Patent: Nov. 11, 2003

(54) REAGENT FOR GPT ASSAY

(75) Inventors: Yoshiro Sato, Koriyama (JP); Chie Satokawa, Koriyama (JP); Ryo Kojima, Koriyama (JP); Katsuhiro Katayama, Koriyama (JP)

(73) Assignee: Nitto Boseki Co., Ltd., Fukishima (JP)

( * ) Notice: Subject to any disclaimer, the term of this patent is extended or adjusted under 35 U.S.C. 154(b) by 0 days.

(21) Appl. No.: 09/805,193

(22) Filed: Mar. 14, 2001

(65) Prior Publication Data

US 2002/0009763 A1 Jan. 24, 2002

(30) Foreign Application Priority Data

Mar. 21, 2000 (JP) ......................................... 2000-078432

(51) Int. Cl.⁷ ................................................. C12Q 1/48
(52) U.S. Cl. ................................ 435/15; 435/16; 435/4
(58) Field of Search ................................. 435/15, 16, 4

(56) References Cited

U.S. PATENT DOCUMENTS 4,235,962 A * 11/1980 Sanderson .................... 435/16
4,547,465 A * 10/1985 Eikenberry .................... 435/15

OTHER PUBLICATIONS

Clinica Chimica Acta, 105 (1980); 147F–154F.

Rinsho Kagaku (Clinical Chemistry), 18(4); Aug. 30, 1989; pp. 250–262, No Tranlsation Provided.

* cited by examiner

*Primary Examiner*—Ralph Gitomer
(74) *Attorney, Agent, or Firm*—Armstrong, Westerman & Hattori, LLP

(57) ABSTRACT

A two reagent-type kit for assaying GPT by acting GPT on L-alanine and α-ketoglutarate in the presence of pyridoxal phosphate, converting the resulting pyruvate into lactate with L-lactate dehydrogenase (LDH) in the presence of reduced nicotinamide adenine dinucleotide (NADH) and measuring GPT based on a decrement of NADH, the GPT assay kit comprising a first reagent and a second reagent, one of which contains pyridoxal phosphate, L-alanine, α-ketoglutarate, LDH and NADH and the other reagent contains no pyridoxal phosphate but contains L-alanine. The GPT assay kit is stable over a long period of time.

2 Claims, 19 Drawing Sheets

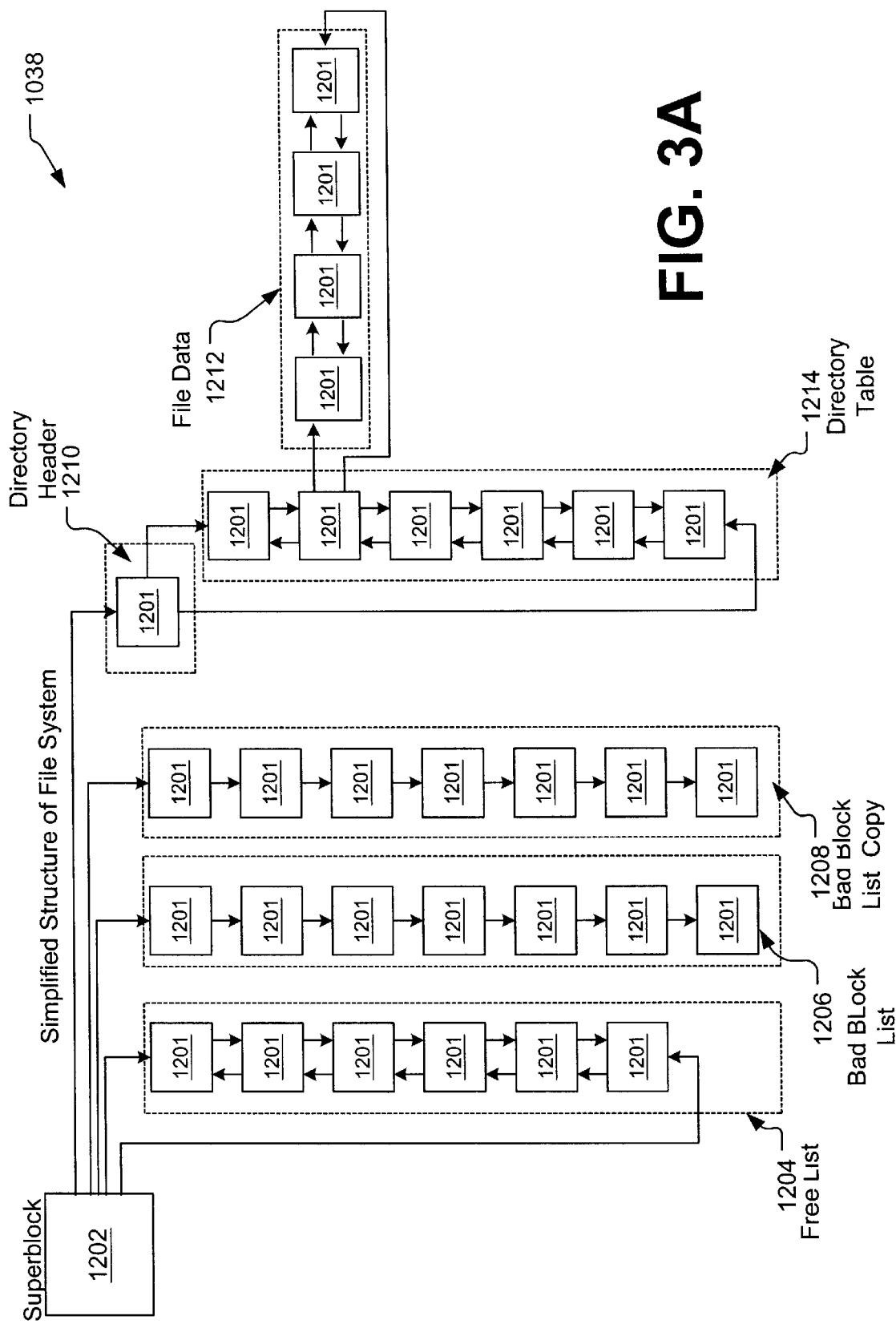

REAGENT FOR GPT ASSAY

BACKGROUND OF THE INVENTION

1. Field of the Invention

Figure 1:
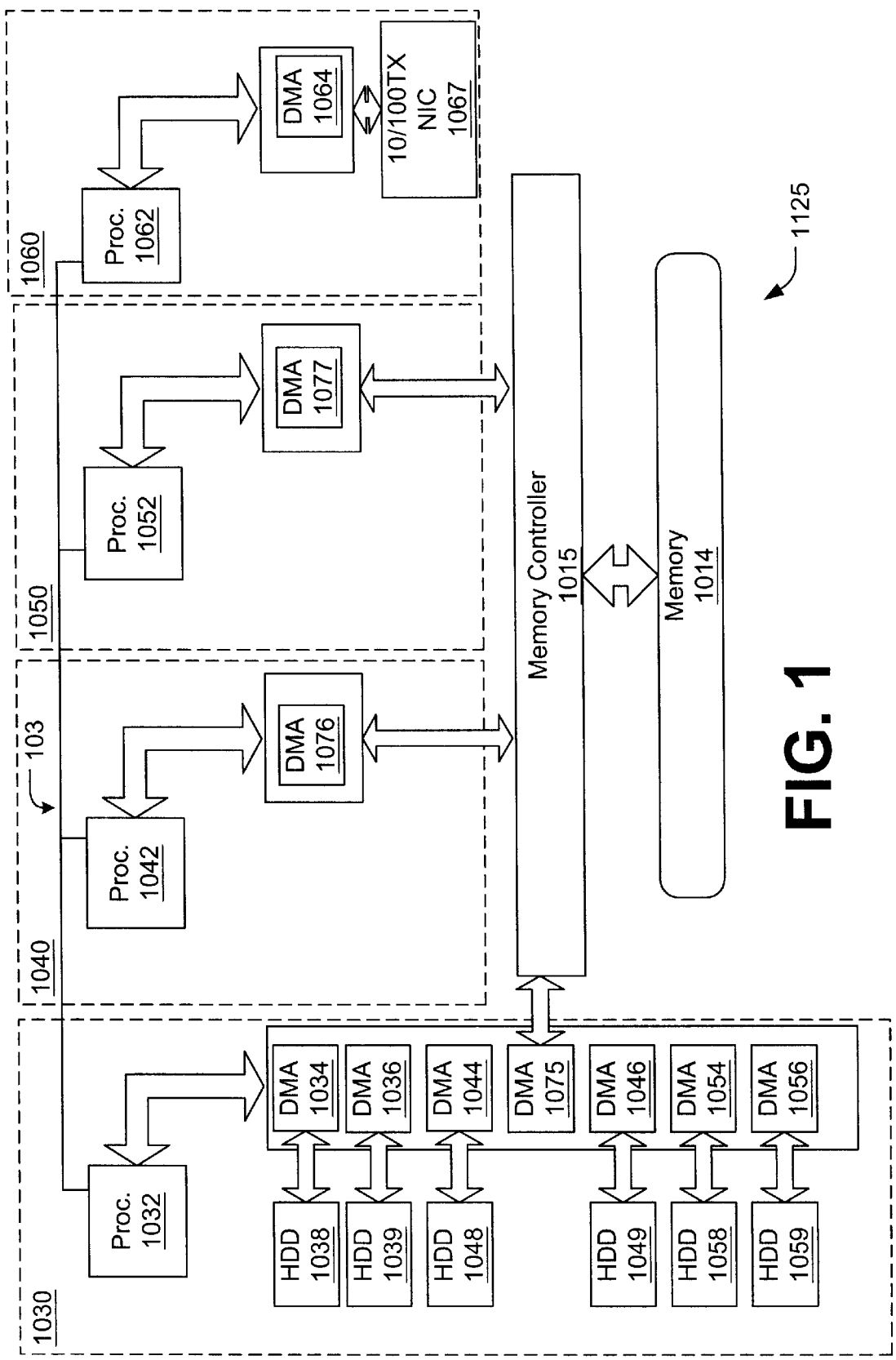

The present invention relates to a reagent kit for assaying glutamic-pyruvic transaminase (hereinafter abbreviated as GPT) and more particularly, to an improved reagent kit for GPT assay which can be stored stably over a long period of time.

2. Description of Related Arts

In routine clinical tests, GPT is one of important items for inspection as a sensitive test method for detecting cell damages or cytotoxicity in various organs, in particular, heart and liver disorders and has been used from old.

For GPT assay, a method called UV method has been widely employed with improved performance of analytical instruments. The UV method comprises acting GPT on L-alanine and α-ketoglutarate as substrate of GPT, converting the resulting pyruvate with L-lactate dehydrogenase (hereinafter abbreviated as LDH) into lactate in the presence of reduced nicotinamide adenine dinucleotide (hereinafter abbreviated as NADH) and measuring a decrement of NADH at a wavelength around 340 nm.

The UV method is expressed by the following equation.

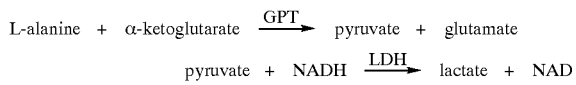

As GPT has become widely assayed, measurement data vary depending upon operator and patient data cannot thus be compared due to lack of interchangeability between measurement data, a problem that there might become an obstacle to diagnosis has begun to emerge. Therefore, assay procedures called recommended assay methods in which reagent concentrations, etc. are prescribed have become proposed in various countries. Internationally, the International Federation of Clinical Chemistry (IFCC) proposed the IFCC method as a standard by acting GPT on L-alanine and α-ketoglutarate in the presence of pyridoxal phosphate (IFCC Scientific Committee: Expert panel on Enzymes, IFCC method for alanine aminotransferase, Clinica Chemica Acta, 105, 147F–157F (1980)). Japan Society of Clinical Chemistry (JSCC) also published the JSCC method for assaying GPT using no pyridoxal phosphate (JSCC: Method for assaying an enzyme activity in human serum—alanine aminotransferase (1989-08-30), Rinsho Kagaku (Clinical Chemistry), 18 (4), 250–262 (1989)).

The IFCC method is compared with the JSCC method and the comparison is shown in Table 1 below.

TABLE 1

| | IFCC Method | JSCC Method |
|---|---|---|
| Reaction temperature | 30° C. | 30° C. |
| Volume of sample | 0.2 mL | 0.3 mL |
| Volume of reagent | 2.4 mL | 3.0 mL |
| Buffer and concentration | Tris 100 mM | Tris 100 mM |
| pH | 7.3 | 7.5 |
| L-Alanine | 500 mM | 500 mM |
| α-ketoglutarate | 15 mM | 15 mM |
| NADH | 0.18 mM | 0.16 mM |
| LDH | 1200 U/L (30° C.) | 2000 U/L (30° C.) |
| Pyridoxal phosphate | 0.1 mM | — |

Pyridoxal phosphate employed in the IFCC method is one of vitamin B6 phosphates and considered to be unstable to heat and light. Pyridoxal phosphate is the most important compound which forms Schiff's base in vivo with ε-amino group of lysine in enzymes (GPT, etc.) that participates in amino acid metabolism and is coupled to GPT to act as a co-enzyme. GPT acts as an enzyme in the form coupled to a co-enzyme but for some reason, the co-enzyme is removed. Such GPT is called apo type GPT. On the other hand, GPT coupled to a co-enzyme is called holo type GPT. Since apo type GPT is activated by adding pyridoxal phosphate to the reagent system, apo type GPT can be assayed together with holo type GPT. Thus, apo and holo type GPTs can be both determined by the IFCC method and the JSCC method, respectively but in the latter method, holo type GPT is mainly assayed because no pyridoxal phosphate is added to the reagent system.

In recent years, techniques to use reagents for clinical test in a liquid state have been improved, which makes it possible to supply stable liquid reagents over a long period of time. In contrast, the liquid reagent system for GPT assay in the presence of pyridoxal phosphate was unsuccessful because pyridoxal phosphate is unstable. At present, there is employed, for example, a reagent kit in which pyridoxal phosphate is provided as a tablet and dissolved in a reagent before use, or a lyophilized reagent. According to the IFCC method, it is prescribed to prepare an aqueous solution of pyridoxal phosphate every 2 weeks. In a solution state, pyridoxal phosphate is colored to yellow the substance inherently possesses but becomes colorless as stability proceeds to deterioration. As such, it is difficult in the existing technique to stabilize pyridoxal phosphate to be used in the GPT assay system over a long period of time. The stability of pyridoxal phosphate is maintained only for a few days after dissolution.

The present inventors have made extensive studies to solve the foregoing problems and as a result have found a reagent composition suitable for GPT assay which has a sufficient storage stability as a liquid reagent. The present invention is based on the finding.

SUMMARY OF THE INVENTION

As a result of expansive investigations on a reagent composition suitable for use in GPT assay, the present inventors have found that among enzymes and substrates to be used, when L-alanine and pyridoxal phosphate are co-present, a yellow color inherent to pyridoxal phosphate is lost during storage and at the same time, measurement data also decreases. Particularly where a reagent kit consists essentially of the two reagents type, a stable reagent GPT assay system can be provided in the form of a two-reagent system kit in which the two substances are isolated from one another, namely, one of the reagents containing pyridoxal phosphate but the other no L-alanine or another reagent containing L-alanine but the other no pyridoxal phosphate.

Therefore, the present invention relates to a kit for assaying glutamic-pyrivic transaminase (GPT) by acting GPT on L-alanine and α-ketoglutarate in the presence of pyridoxal phosphate, converting the resulting pyruvate into lactate with L-lactate dehydrogenase (LDH) in the presence of reduced nicotinamide adenine dinucleotide (NADH) and measuring GPT based on a decrement of NADH, the GPT assay kit:

1) being of a two reagent type kit comprising a first reagent and a second reagent wherein:
2) one of the first and second reagents contains pyridoxal phosphate, L-alanine, α-ketoglutarate, LDH and NADH as essential components; and,
3) one of the reagents free of L-alanine contains pyridoxal phosphate and the other reagent free of pyridoxal phosphate contains L-alanine.

DETAILED DESCRIPTION OF THE INVENTION

Hereinafter the invention will be described in detail.

The GPT assay kit of the invention relates to an assay kit of two reagents type comprising a first reagent and a second reagent, in which one of the reagents contains pyridoxal phosphate but no L-alanine and another reagent contains L-alanine but no pyridoxal phosphate.

The GPT assay kit of the invention may be in a lyophilized form but even in a liquid form, can keep its stability over a long period of time so that the yellow color inherent to pyridoxal phosphate can also be maintained over long time.

In general, it is preferred to prepare, as a first reagent, a composition comprising pyridoxal phosphate, LDH and NAPDH as essential components and as a second reagent, a composition comprising L-alanine and α-ketoglutarate as essential components and prepare the two compositions into a kit. LDH and NADH as a co-enzyme of LDH which are incorporated in the first reagent are advantageous in canceling pyruvate in a sample, since the pyruvate causes a measurement error.

The first reagent free of L-alanine and containing pyridoxal phosphate is designed to have a pH range preferably from 7 to 10. It is also advantageous for the second reagent to have a pH range between 7 and 8, preferably approximately 7.3, when GPT acts. Such a preferred pH range for GPT is provided by adjusting the second reagent and a buffer to an appropriate pH and concentration, respectively, followed by mixing the thus adjusted second reagent and buffer with the first reagent. By preparing the first and second reagents having an adjusted pH range as above, the respective components contained in the first and second compositions can be maintained stably over a long period of time.

Any known buffer solution may be employed as the buffer for the first reagent so long as its pH can be adjusted within the range given above. More specifically, tris (hydroxymethyl)aminomethane used in the IFCC method and the JSCC method as well as a buffer solution having a buffering function in a pH range of 7 to 10 may be freely used in the invention. The pH of the first reagent may be adjusted to a range of 7 to 10 by combining a plurality of buffer solutions. As described above, the first reagent preferably has a pH in the range of 7 to 10, more preferably 8.5 to 9.0.

Known buffer solutions may be appropriately chosen and used as a buffer for the second reagent to adjust the pH upon the GPT reaction to the range given above. More specifically, tris(hydroxymethyl)aminomethane may be used as in the first reagent. The pH range for the buffer solution is not particularly limited. Preferably, the pH and concentration of the buffer solution are adjusted to provide pH range between 7 and 8 when mixed with the first reagent.

In the first reagent, pyridoxal phosphate is incorporated generally in an amount of 0.01 to 1 mM, preferably 0.1 to 0.3 mM. NADH is used generally in an amount of 0.05 to 5 mM, preferably 0.1 to 1 mM. The source of LDH used in the invention is not particularly limited. LDH is incorporated appropriately to have a concentration of 1000 U or more.

L-Alanine used in the second reagent is incorporated generally in an amount of 10 to 2000 mM, preferably 500 to 1500 mM. α-Ketoglutarate is added generally in an amount of 1 to 200 mM, preferably 10 to 50 mM.

The amounts of these reagents are not strict and may thus be outside the ranges above, since they may vary depending on a mixing ratio of the first and second reagents.

The first and second reagents may appropriately contain, if necessary and required, other conventional additives, e.g., a chelating agent such as EDTA, an antiseptic such as sodium azide, various surfactants, etc.

By assaying GPT in a sample using the GPT assay kit thus constructed, GPT in the sample is activated by the action of pyridoxal phosphate from apo type GPT into holo type GPT. L-Alanine and α-ketoglutarate as substrate of GPT are acted on holo type GPT present in the sample to produce glutamate and pyruvate. By the action of LDH as a coupling enzyme, pyruvate oxidizes NADH to produce lactate and NAD. A decreased amount of NADH which is oxidized by the above reaction is measured in terms of absorbance at a wavelength of about 340 nm to determine the GPT activity.

The present invention will be described below in more detail with reference to the following examples but is not deemed to be limited to thereto.

EXAMPLE 1

Stability of Pyridoxal Phosphate to L-alanine

Stability of pyridoxal phosphate to L-alanine was examined.

Pyridoxal phosphate was added in an amount of 0.125 mM to 36.6 mM Tris (hydroxymethyl) aminomethane buffer (pH 8.70), to which LDH, β-NADH and a surfanctant were added. L-Alanine was added to the mixture in an amount of 200 mM or 400 mM and pH was adjusted to 8.70 with 4N-NaOH to prepare a first reagent. For control, L-alanine-free first reagent was prepared in a similar manner.

A second reagent was prepared by adding L-alanine, α-ketoglutarate and a surfactant to 366 mM Tris (hydroxymethyl)aminomethane buffer (pH 4.00) and then adjusting pH of the mixture with 2N-HCl. Compositions of the first and second reagents are shown below.

| Composition of the first reagent | | |
|---|---|---|
| Tris(hydroxymethyl)aminomethane | 36.6 mM | pH 8.70 |
| β-NADH | 0.02 mM | |
| LDH | 2567 U/L | |
| Surfactant | 0.01% | |
| Pyridoxal phosphate | 0.125 mM | |
| L-Alanine | 0, 200 or 400 mM | |
| Composition of the second reagent | | |
| Tris(hydroxymethyl)aminomethane | 366 mM | pH 4.00 |
| α-ketoglutarate | 77 mM | |
| L-Alanine | 1000 mM | |
| Surfactant | 0.01% | |

The GPT activity was determined using an automated analyzer of Hitachi Model 7150 (Hitachi 717) by acting 300 μL of the first reagent and 75 μL of the second reagent on 10 μL of serum or physiological saline as a sample to adjust to the main wavelength at 340 nm and secondary wavelength at 405 nm and tracing a change in absorbance between 30–50 data points (which correspond to 1–5 minutes after addition of R2). The GPT activity in the sample was calculated according to the following equation:

$$\text{GPT activity } (IU/L) = (\Delta E/\text{min})/\epsilon \times (V/v) \times 10^6$$

ΔE/min: change in absorbance per minute

ε: molar extinction coefficient ($6.22 \times 10^3$ L/mol.cm in NADH)

V: total volume (sample+first reagent+second reagent)

v: volume of a sample

The stability of pyridoxal phosphate was determined by calculating a change in measurement data when the measurement data of control serum was made 100% on the day it was prepared and the first reagent was stored at 4° C. and 37° C. The results are shown in Table 2. The stability was also evaluated in terms of change in color of pyridoxal phosphate. The results are shown in Table 3.

TABLE 2

Change in measurement data of control serum during storage at 37° C.

| Passage of time (day) | Concentration of L-alanine in the first reagent | | |
|---|---|---|---|
| | 0 mM | 200 mM | 400 mM |
| 0 | 100% | 100% | 100% |
| 6 | 99% | 99% | 96% |
| 15 | 98% | 78% | 80% |

Table 2 shows the measurement data of control serum in terms of relative activity as compared to the activity measured on the day when the serum sample was prepared. As shown in Table 2, when L-alanine was added to the first reagent in which L-alanine was co-present with pyridoxal phosphate, the measurement data decreased every assay day during storage at 37° C., indicating that the stability of the reagent was being lost. In the reagent added with no L-alanine, measurement data hardly changed even when the reagent was stored at 37° C., indicating that the reagent maintained its stability.

TABLE 3

Change in color of the first reagent during storage at 37° C.

| Passage of time (day) | Concentration of L-alanine in the first reagent | | |
|---|---|---|---|
| | 0 mM | 200 mM | 400 mM |
| 0 | ++ | ++ | ++ |
| 2 | ++ | ++ | + |
| 4 | ++ | + | − |
| 6 | ++ | − | − |
| 15 | ++ | − | − |

In the table above, symbols "++", "+" and "−" denote yellow, light yellow and colorless. Table 3 also indicates that when L-alanine was present in the reagent, the color was lost to the colorless state regardless of concentration, with a surmise that pyridoxal phosphate would change. In contrast, in the reagent free of L-alanine, the initial color was kept. That is, these results clearly indicate that the stability of pyridoxal phosphate is lost in the co-presence of L-alanine and the L-alanine-free reagent but containing pyridoxal phosphate is excellent in terms of stability.

EXAMPLE 2

Stability of Pyridoxal Phosphate to pH

A change in stability of pyridoxal phosphate to pH was examined.

After 0.205 mM pyridoxal phosphate was added to 100 mM Tris(hydroxymethyl)aminomethane buffer, LDH, β-NADH, sodium chloride and a surfactant were further added to the mixture followed by adjusting pH of the reagent with 4N-NaOH and 2N-HCl in the range of 7 to 10, which was made a first reagent. A second reagent was prepared by adding L-alanine and α-ketoglutarate to 105 mM Tris (hydroxymethyl)aminomethane buffer (pH 4.20) and adjusting the pH with 2N-HCl. The first and second reagents have the following compositions.

| Composition of the first reagent | | |
|---|---|---|
| Tris(hydroxymethyl)aminomethane | 100 mM | pH 7, 8, 9 or 10 |
| Sodium chloride | 100 mM | |
| EDTA.2Na | 0.2 mM | |
| β-NADH | 0.369 mM | |
| LDH | 2460 U/L | |
| Surfactant | 0.01% | |
| Pyridoxal phosphate | 0.205 mM | |
| Composition of the second reagent | | |
| Tris(hydroxymethyl)aminomethane | 105 mM | pH 4.2 |
| α-ketoglutarate | 30.75 mM | |
| L-Alanine | 1025 mM | |
| Surfactant | 0.01% | |

The GPT activity was determined using an automated analyzer of Hitachi Model 7150 by acting 200 μL of the first reagent and 200 μl of the second reagent on 10 μL of serum or physiological saline as a sample, in which the main wavelength was set at 340 nm and the secondary wavelength at 405 nm, and tracing a change in absorbance between 30–50 data points (which correspond to 1–5 minutes after addition of R2). The GPT activity was calculated as in Example 1.

The stability of pyridoxal phosphate was determined with the first reagent stored at 37° C. as in Example 1 by calculating a change in measurement data when the measurement data of control serum was made 100% on the day it was prepared. The results are shown in Table 4. The stability was also evaluated in terms of change in the color of pyridoxal phosphate. The results are shown in Table 5.

TABLE 4

Change in measurement data of control serum during storage at 37° C.

| Passage of time (day) | pH of the first reagent | | | |
|---|---|---|---|---|
| | pH 7 | pH 8 | pH 9 | pH 10 |
| 0 | 100% | 100% | 100% | 100% |
| 6 | 99% | 98% | 99% | 99% |
| 15 | 97% | 99% | 100% | 95% |

Table 4 shows the measurement data of control serum in terms of relative activity as compared to the activity measured on the day when the serum sample was prepared. As shown in Table 4, the measurement data of the control serum did not appreciably change in pH of from 7 to 10, especially 7 to 9, showing that the reagent was stable.

TABLE 5

Change in color of the first reagent during storage at 37° C.

| Passage of time (day) | pH of the first reagent | | | |
|---|---|---|---|---|
| | pH 7 | pH 8 | pH 9 | pH 10 |
| 0 | ++ | ++ | ++ | + |
| 2 | ++ | ++ | ++ | + |
| 4 | ++ | ++ | ++ | + |
| 6 | ++ | ++ | ++ | + |
| 15 | ++ | ++ | ++ | + |

In the table above, symbols "++", "+" and "−" denote yellow, light yellow and colorless. It is understood from Table 5 that the first reagent maintained the color in pH between 7 and 10, especially between 7 and 9, demonstrating that the stability of pyridoxal phosphate was maintained especially in the pH range of 7 to 9.

As shown in the Examples above, the reagent composition of the invention can be provided in a liquid state when it is applied to an automated analyzer, accompanied by markedly improved operability and stability. That is, according to the present invention, not only the stability of pyridoxal phosphate can be maintained in a liquid form that could not be achieved by the prior art, but the reagent composition usable over a long period of time can be provided.

What is claimed is:

1. A two reagent kit for assaying glutamic-pyruvic transaminase (GPT) by reacting GPT with L-alanine and α-ketoglutarate in the presence of pyridoxal phosphate, converting the resulting pyruvate into lactate with L-lactate dehydrogenase (LDH) in the presence of reduced nicotinamide adenine dinucleotide (NADH) and measuring GPT based on a decrease of NADH, the kit for assaying GPT:

1) comprising a first reagent and a second reagent, said first reagent and said second reagent being in liquid form, wherein:
   2) the first reagent contains pyridoxal phosphate, LDH and NADH, and has a pH in the range of 8.5 to 9.0; and
   3) the second reagent contains L-alanine and α-ketoglutarate, and has such a pH that a liquid prepared by mixing the second reagent with the first reagent to measure GPT will have pH in the range of 7 to 8.

2. A kit for assaying GPT according to claim 1, wherein the second reagent has a pH such that a liquid prepared by mixing the second reagent with the first reagent to measure GPT will have a pH of approximately 7.3.

* * * * *

UNITED STATES PATENT AND TRADEMARK OFFICE
CERTIFICATE OF CORRECTION

| | | |
|---|---|---|
| PATENT NO. | : 6,645,735 B2 | Page 1 of 1 |
| DATED | : November 11, 2003 | |
| INVENTOR(S) | : Yoshio Sato et al. | |

Figure 2:
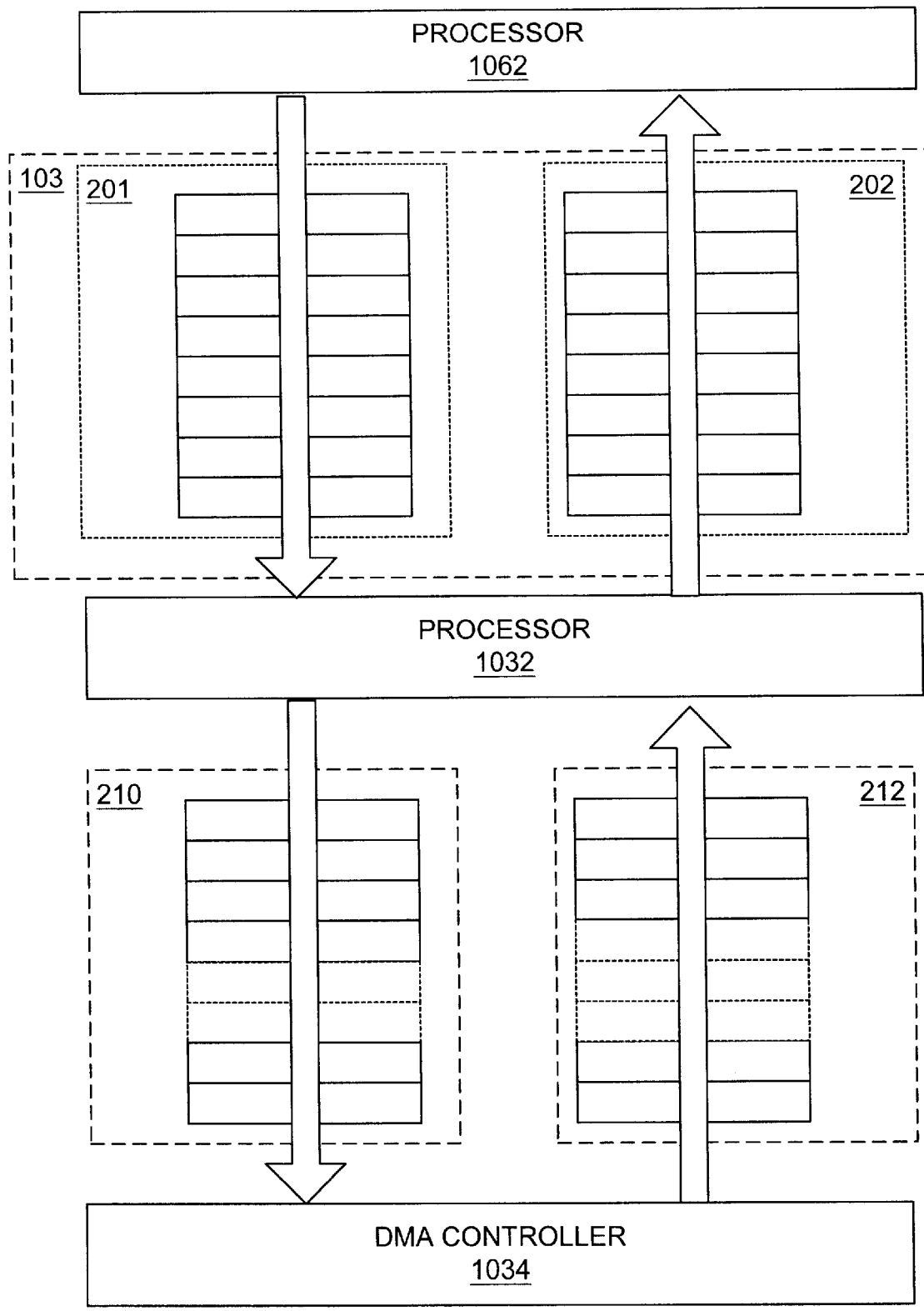
Figure 3B:
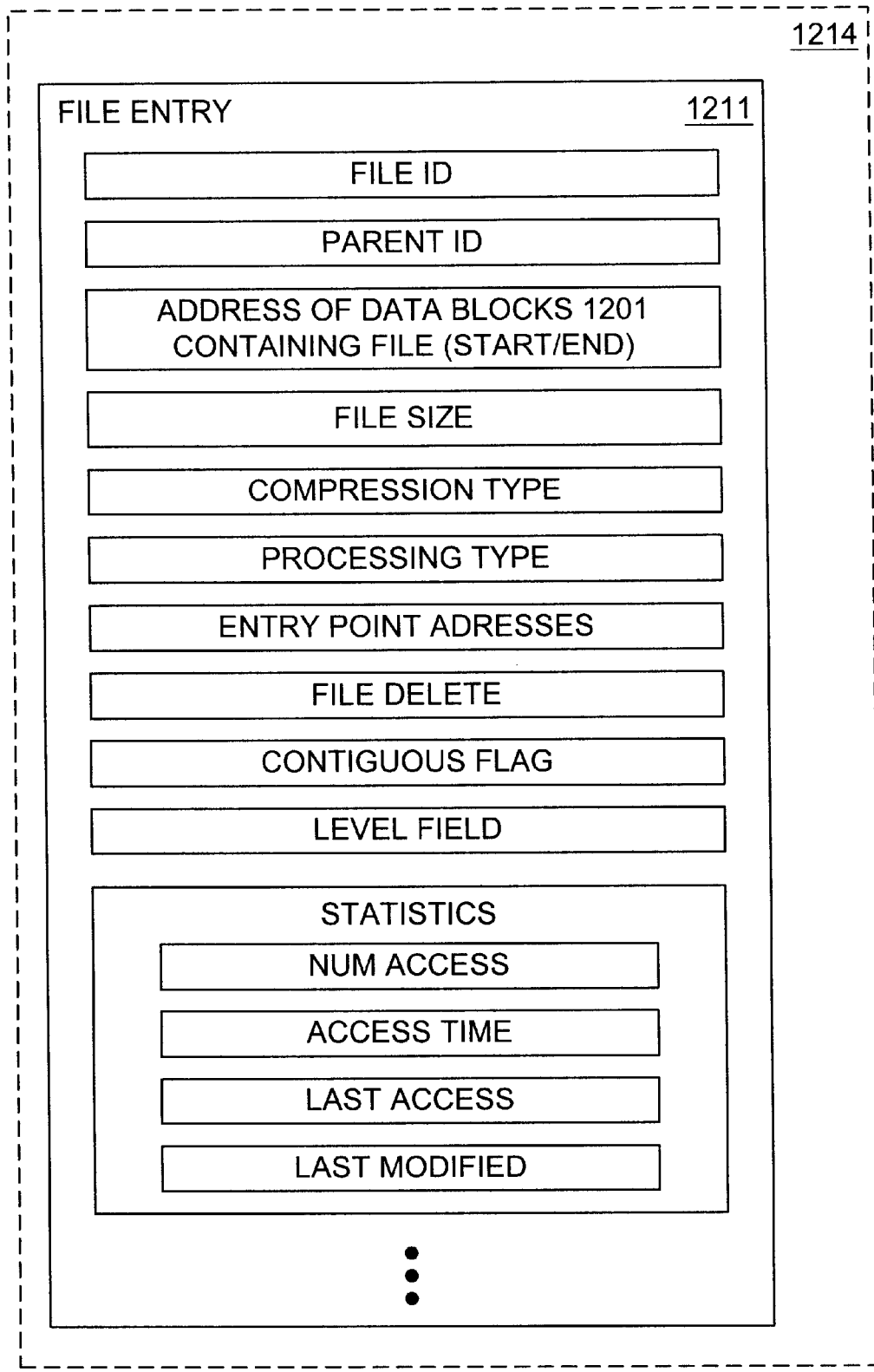
Figure 3C:
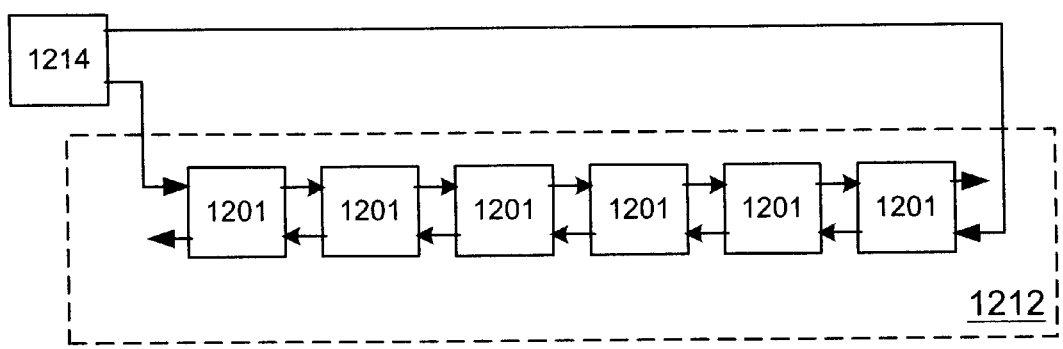
Figure 4A:
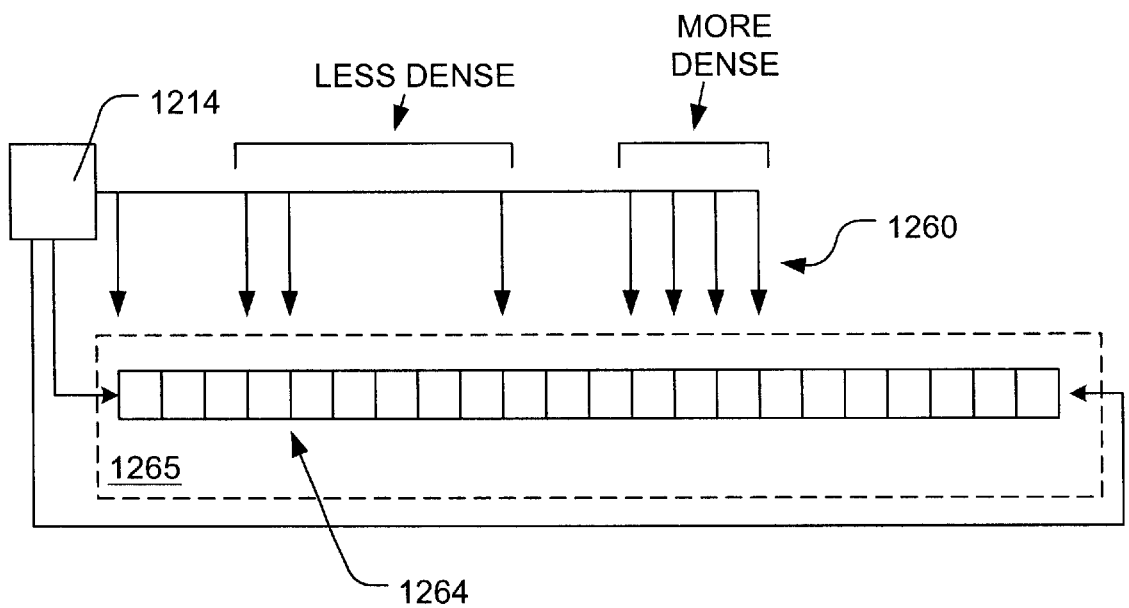
Figure 4B:
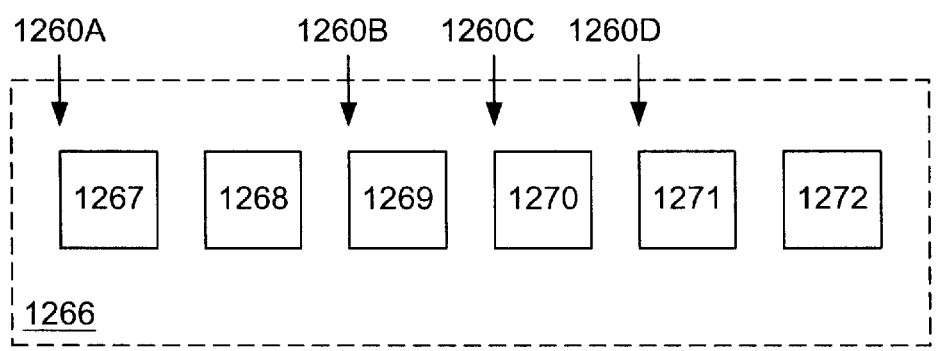
Figure 5:
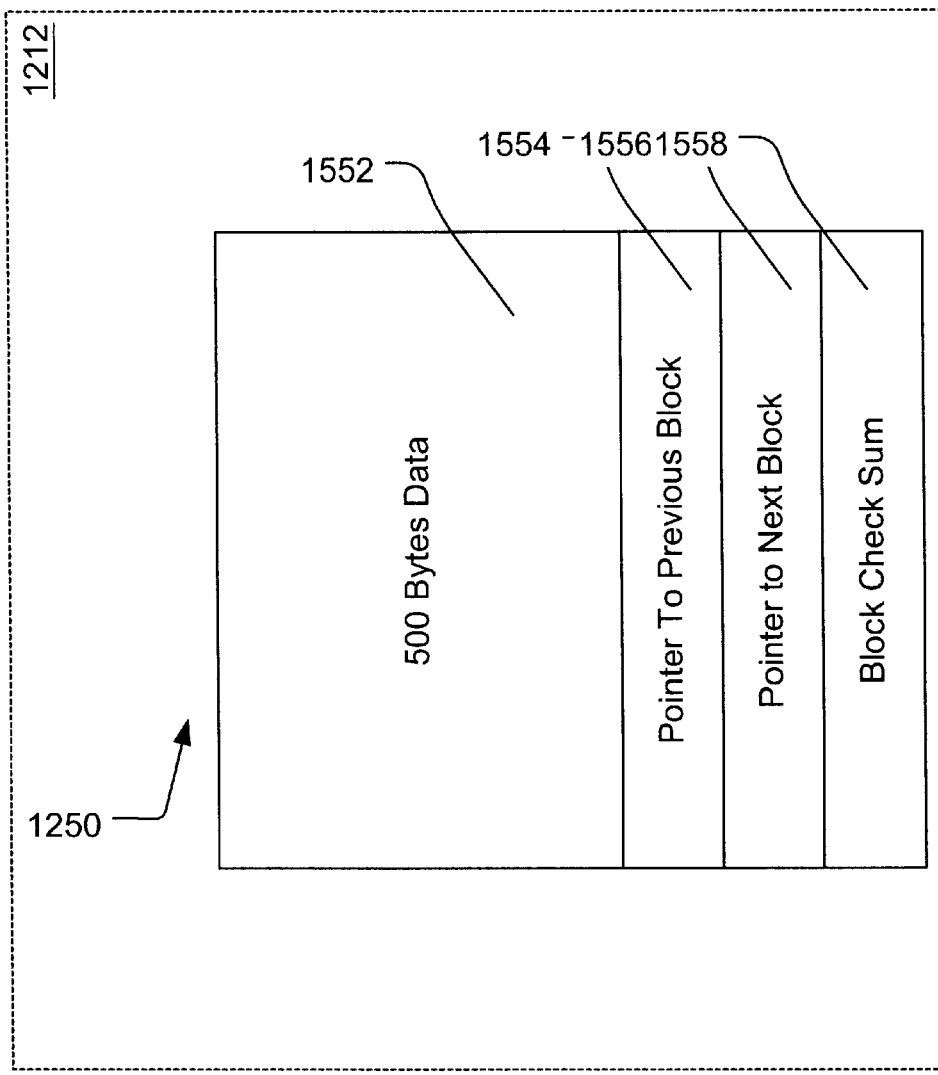
Figure 6:
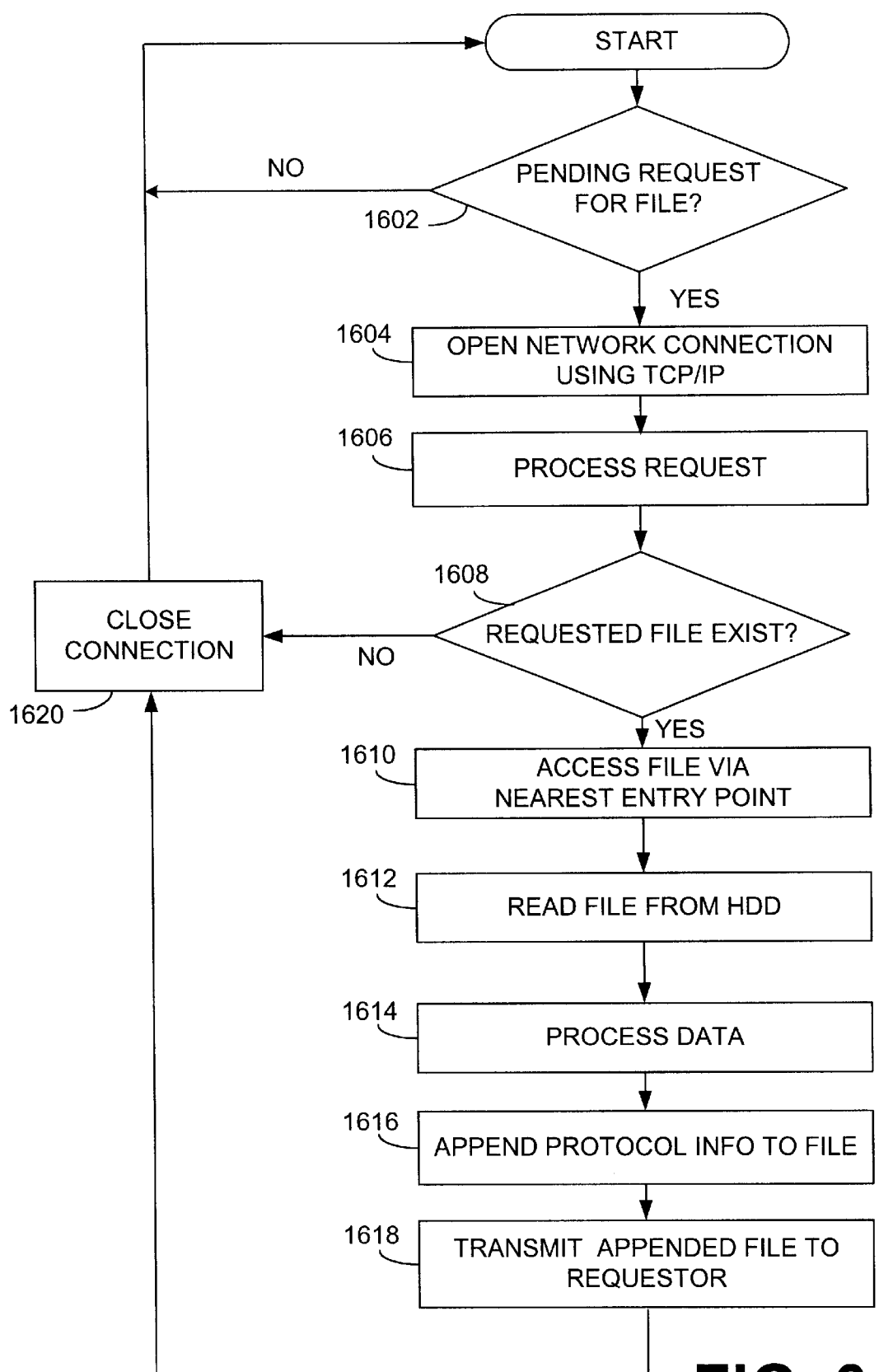
Figure 7:
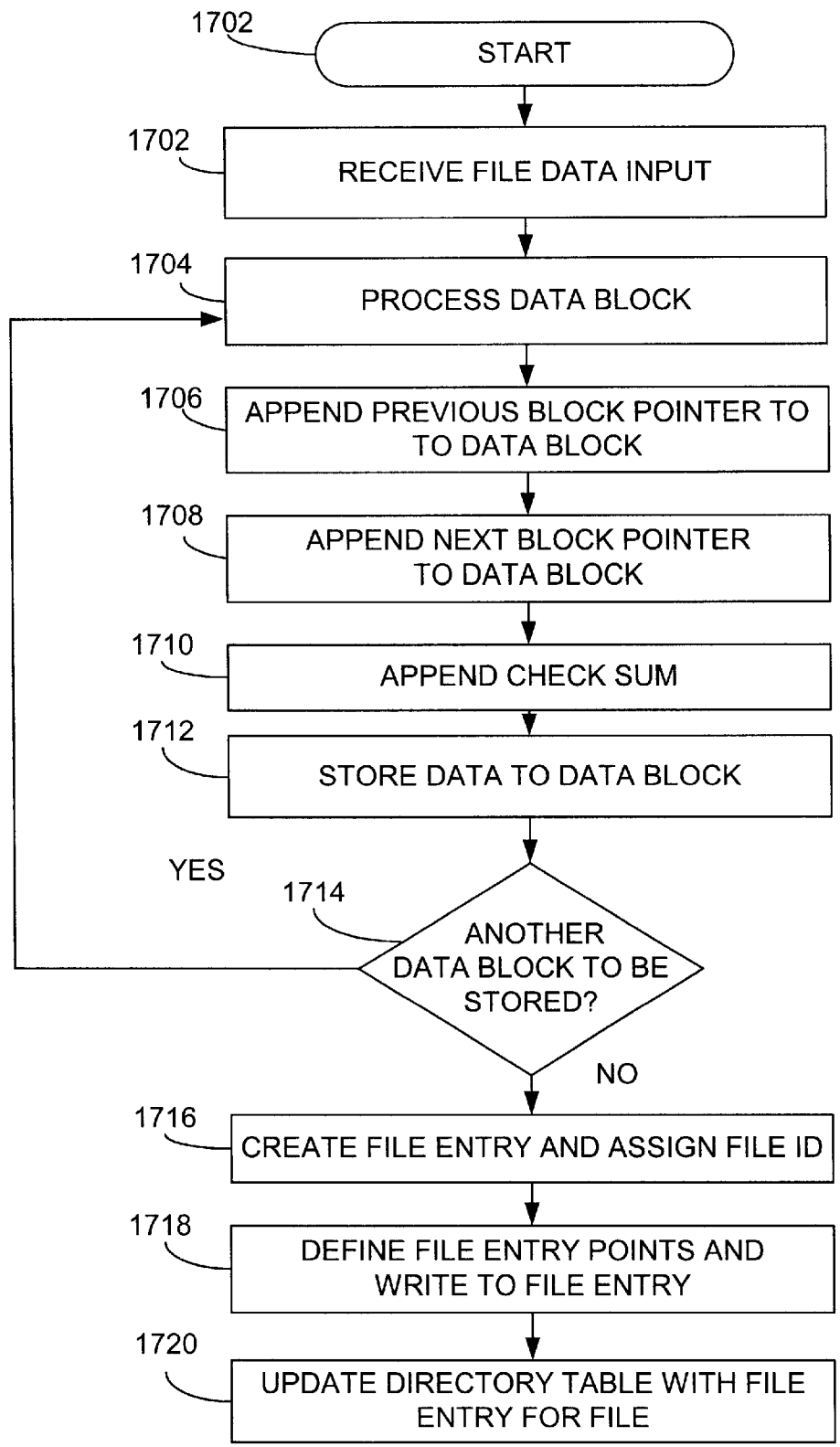
Figure 8:
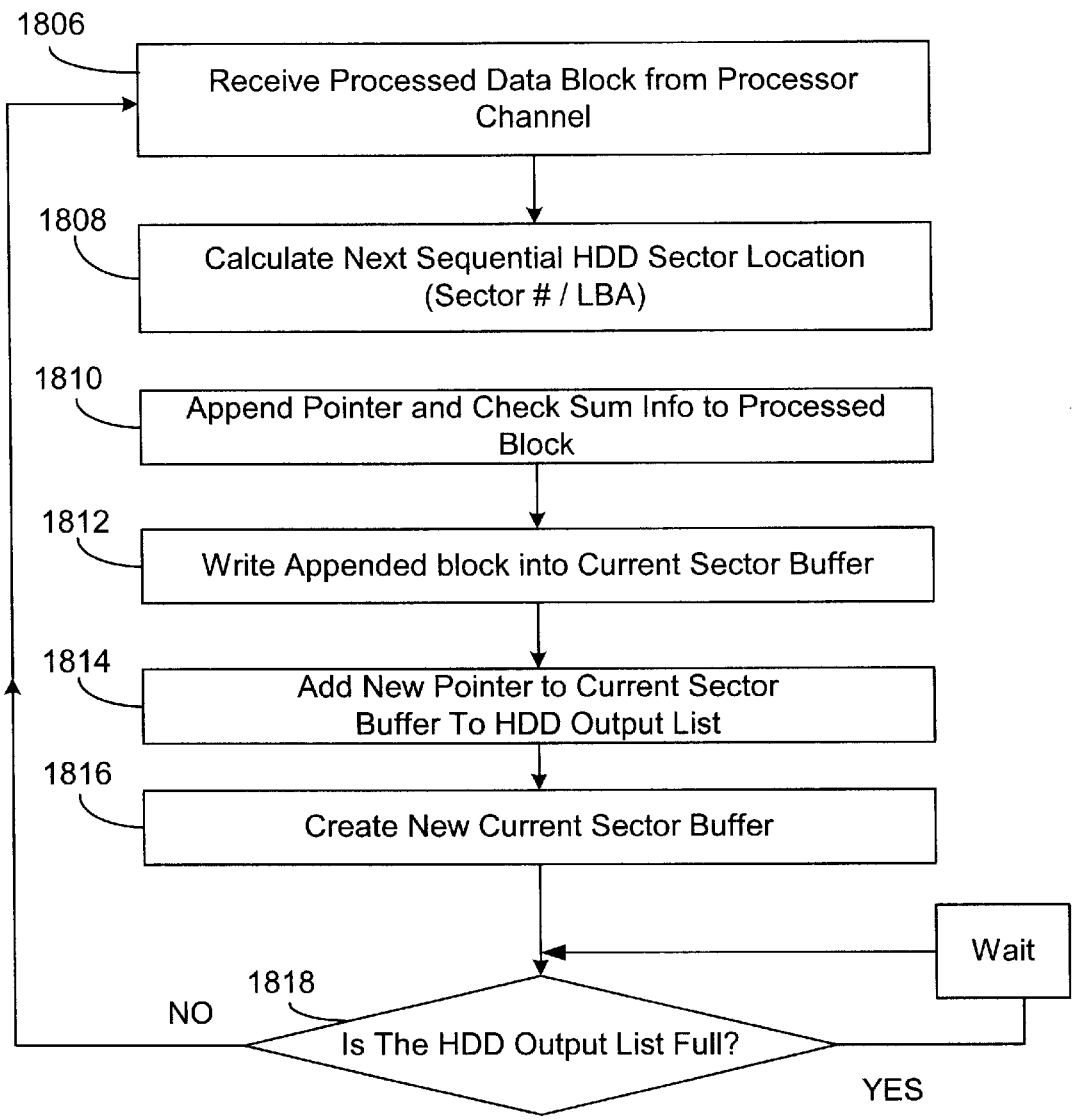
Figure 9:
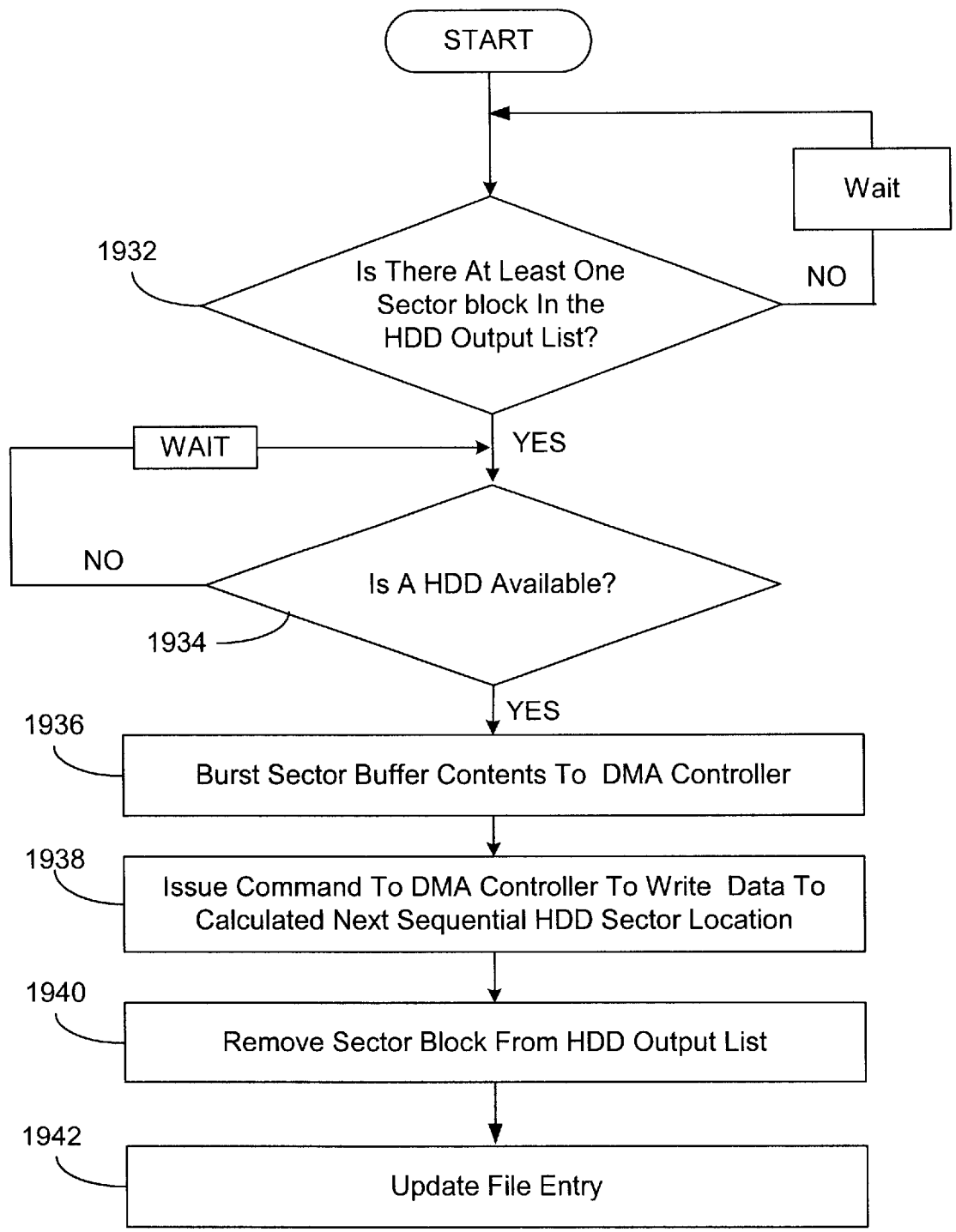
Figure 10A:
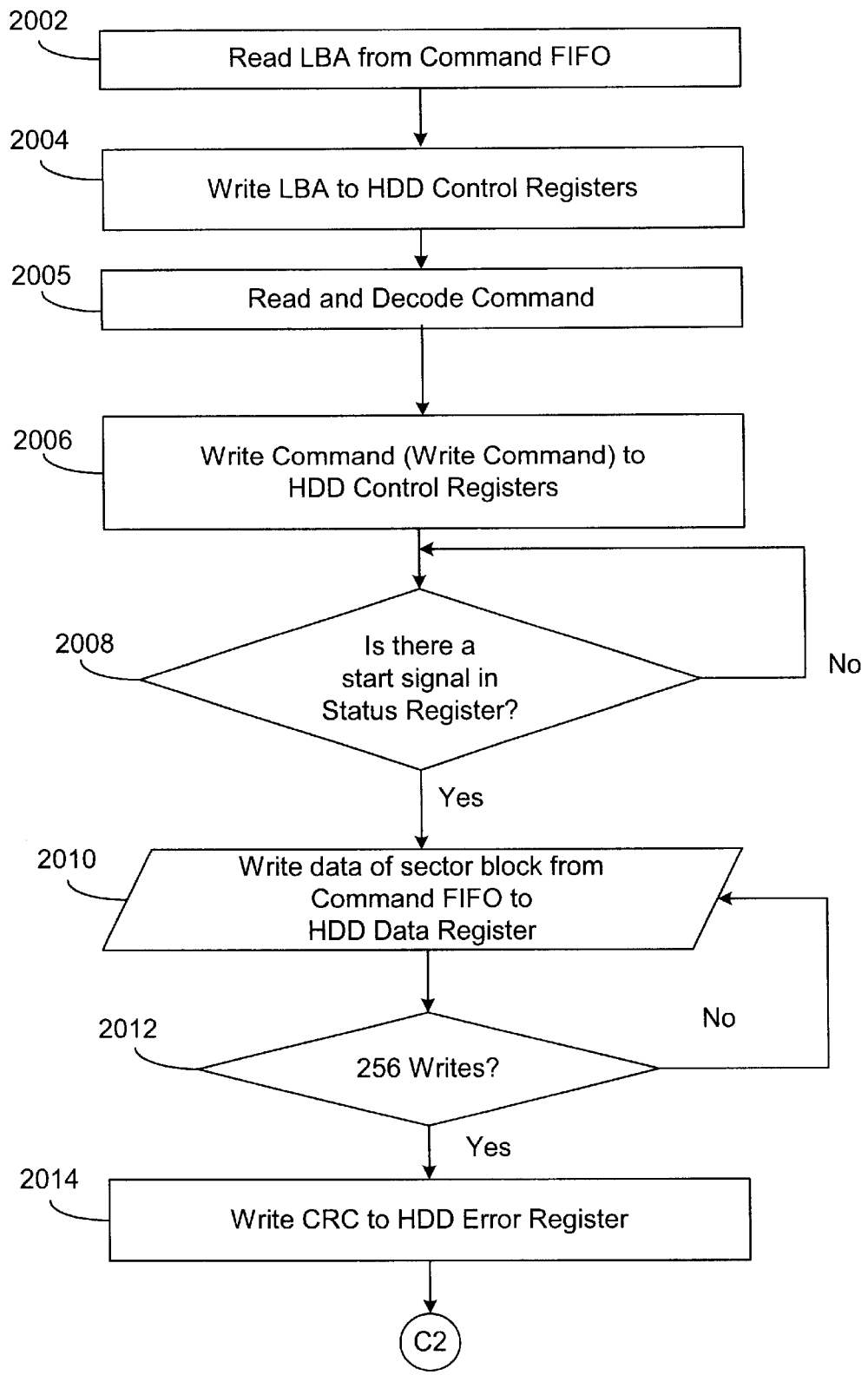
Figure 10B:
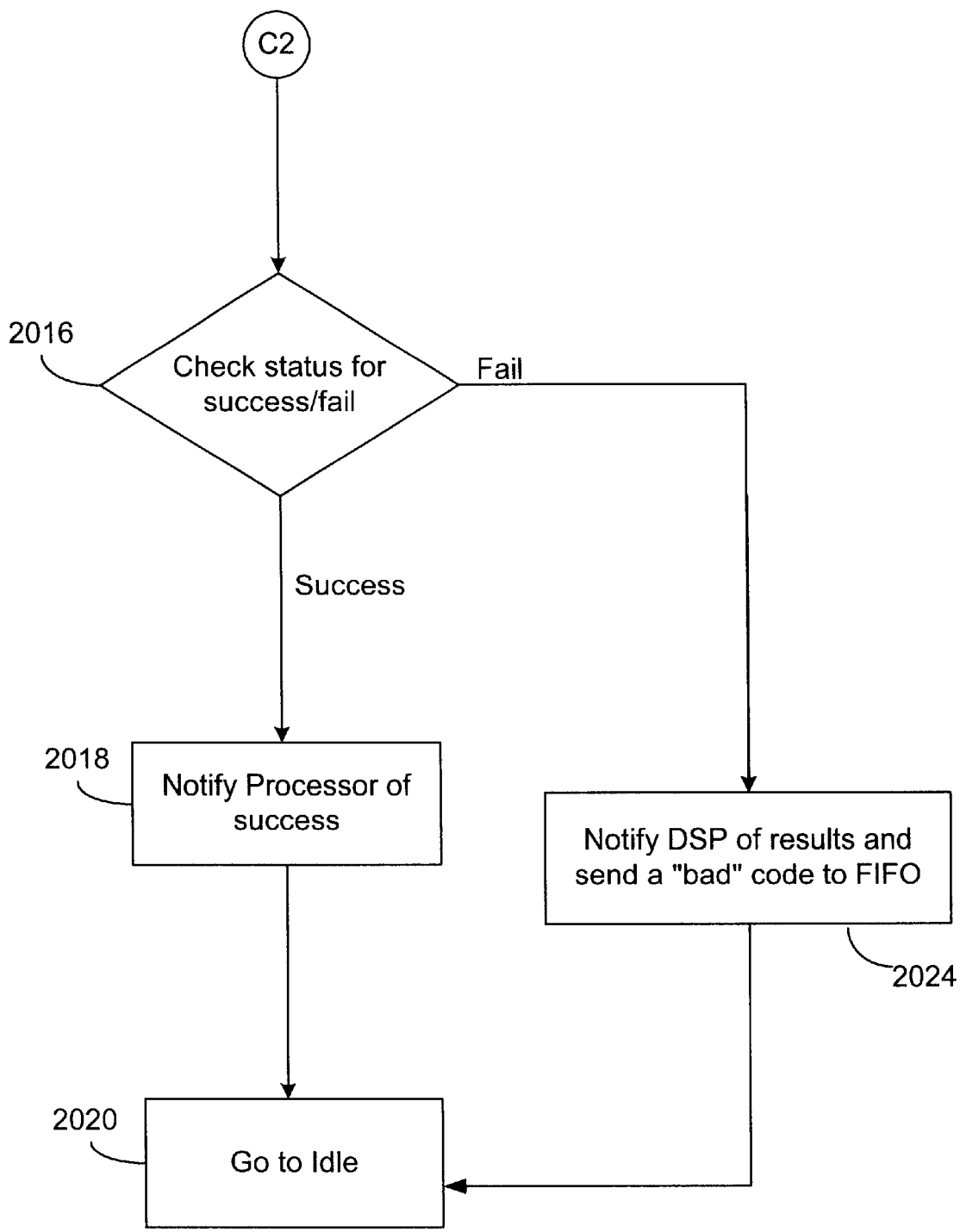
Figure 10C:
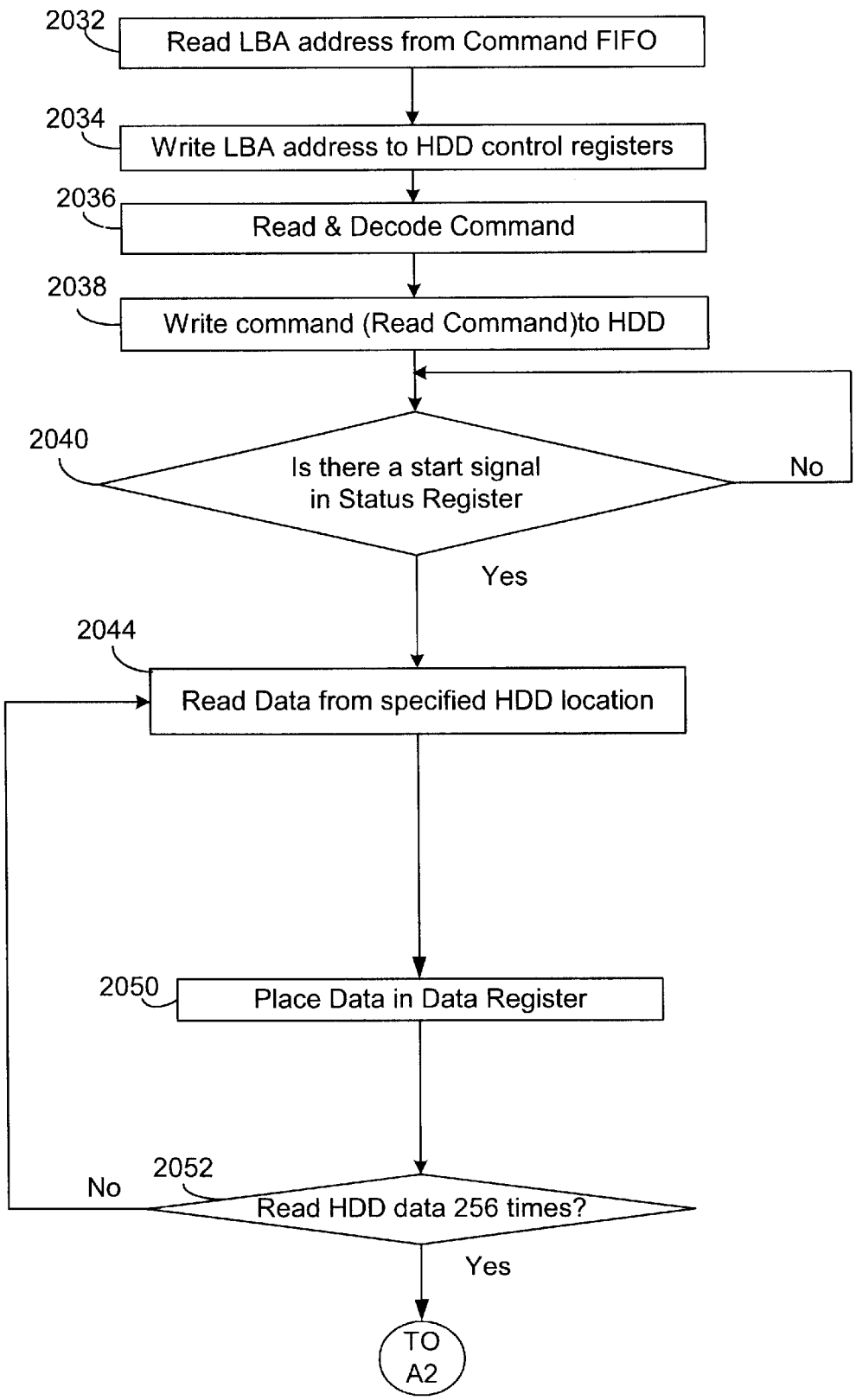
Figure 10D:
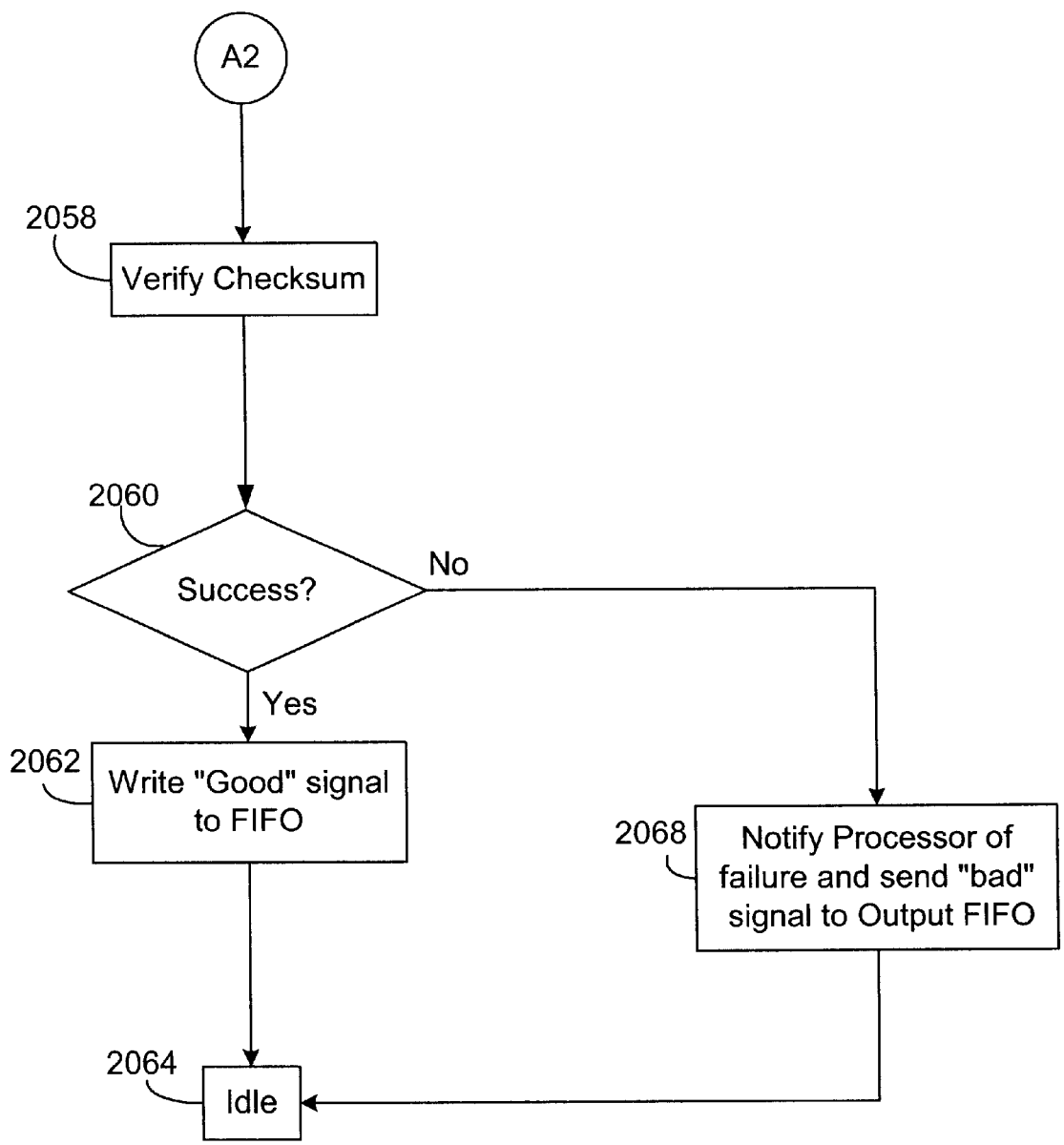
Figure 11:
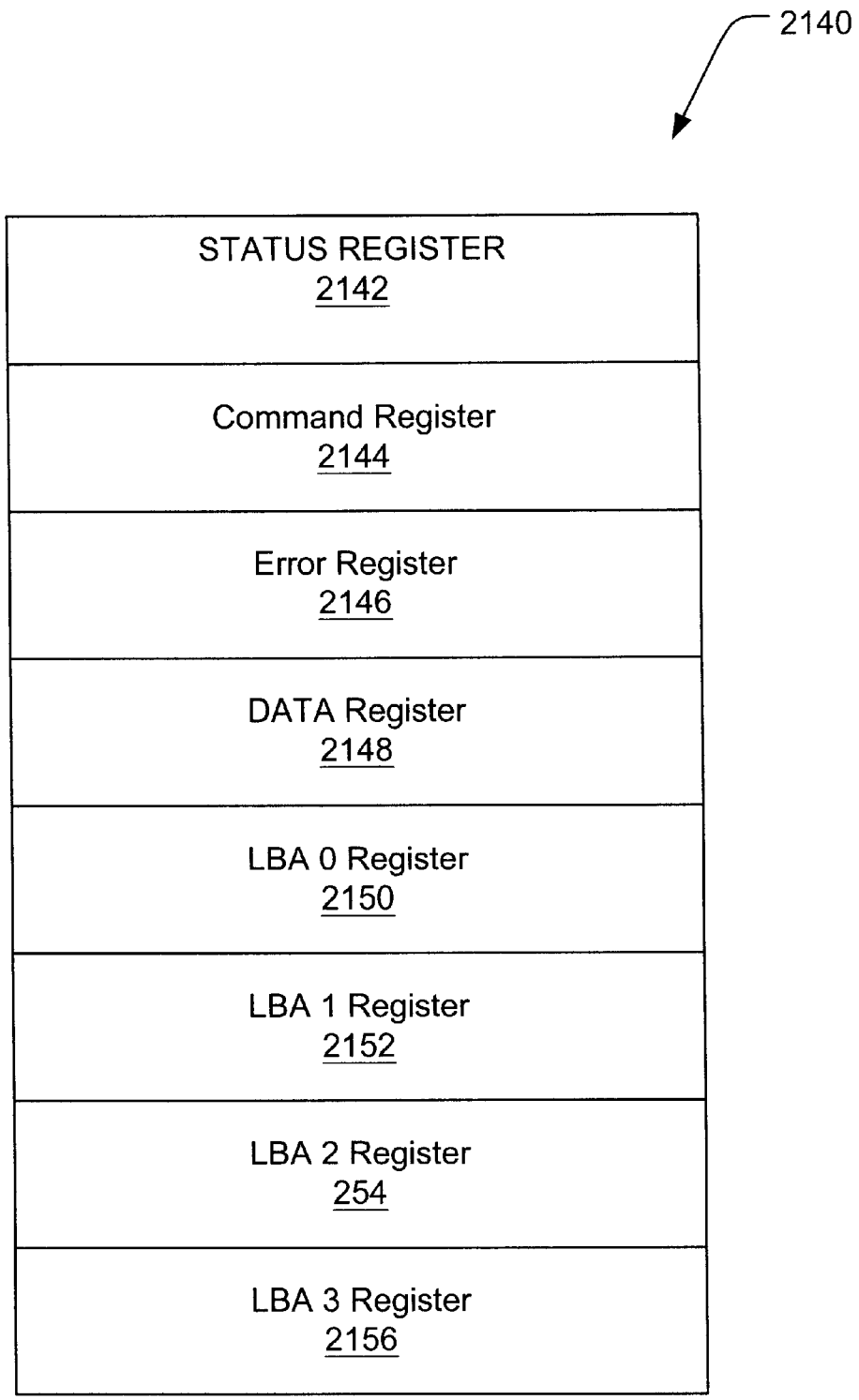
Figure 12:
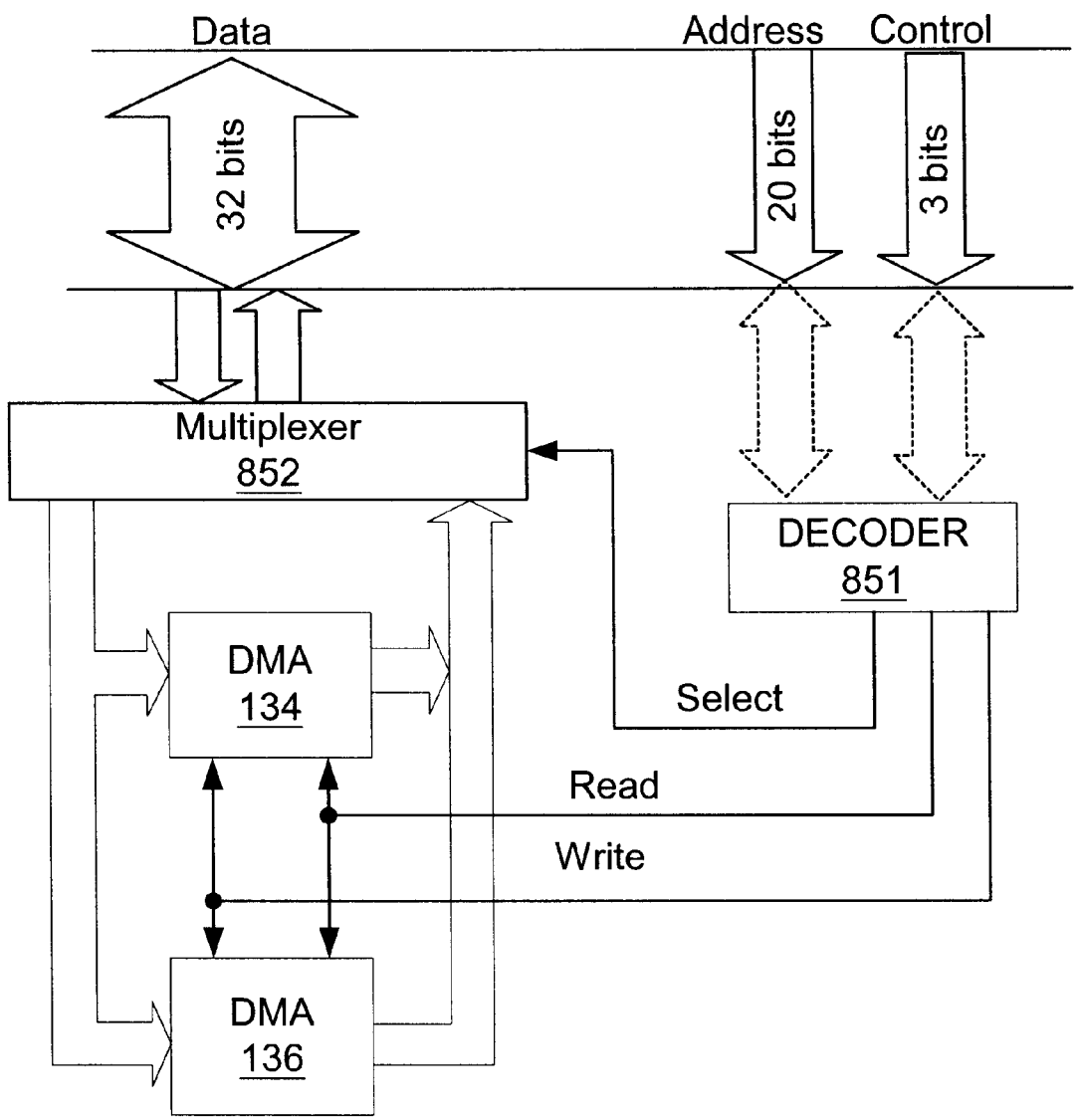
Figure 13:
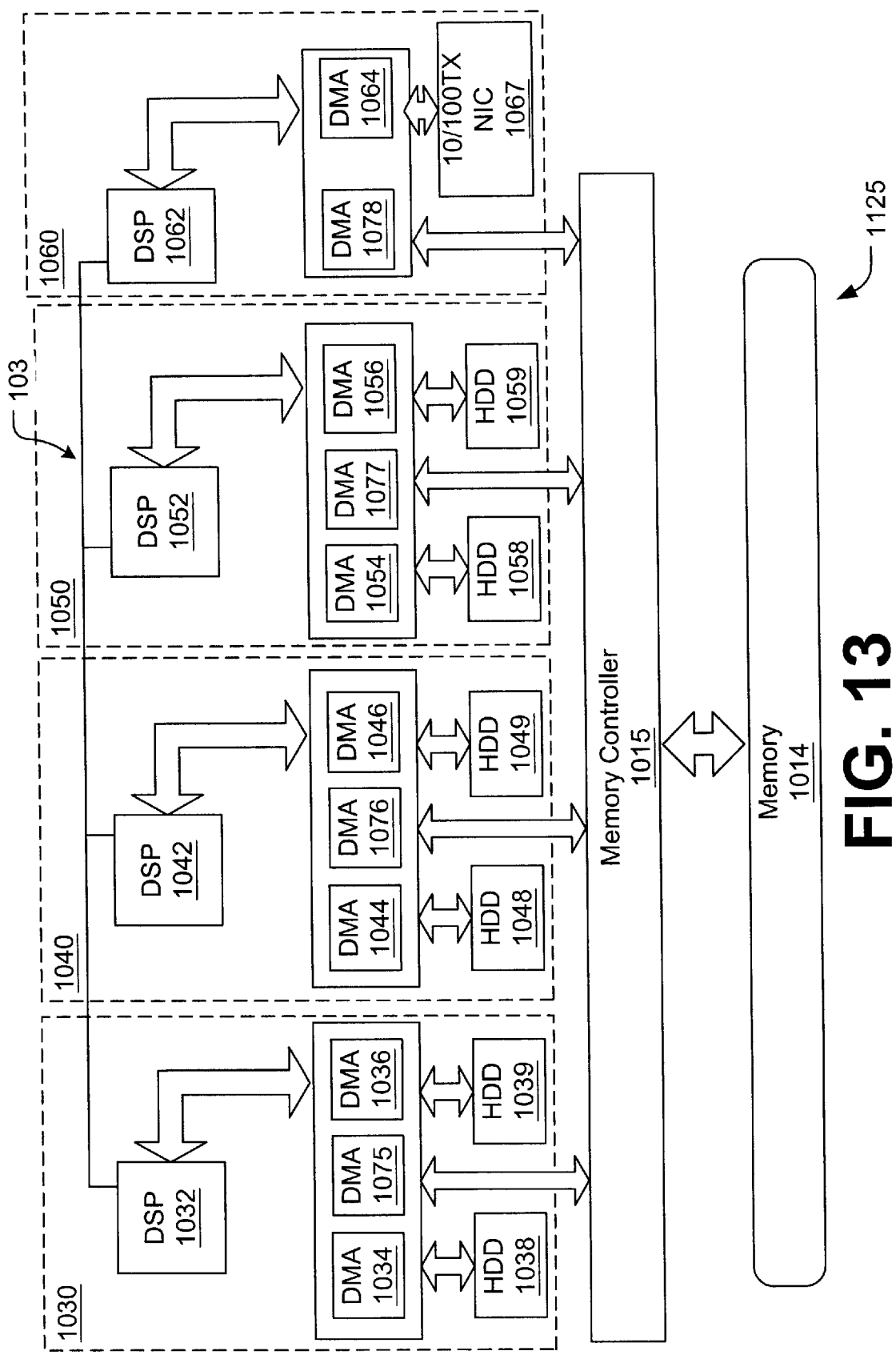
Figure 14:
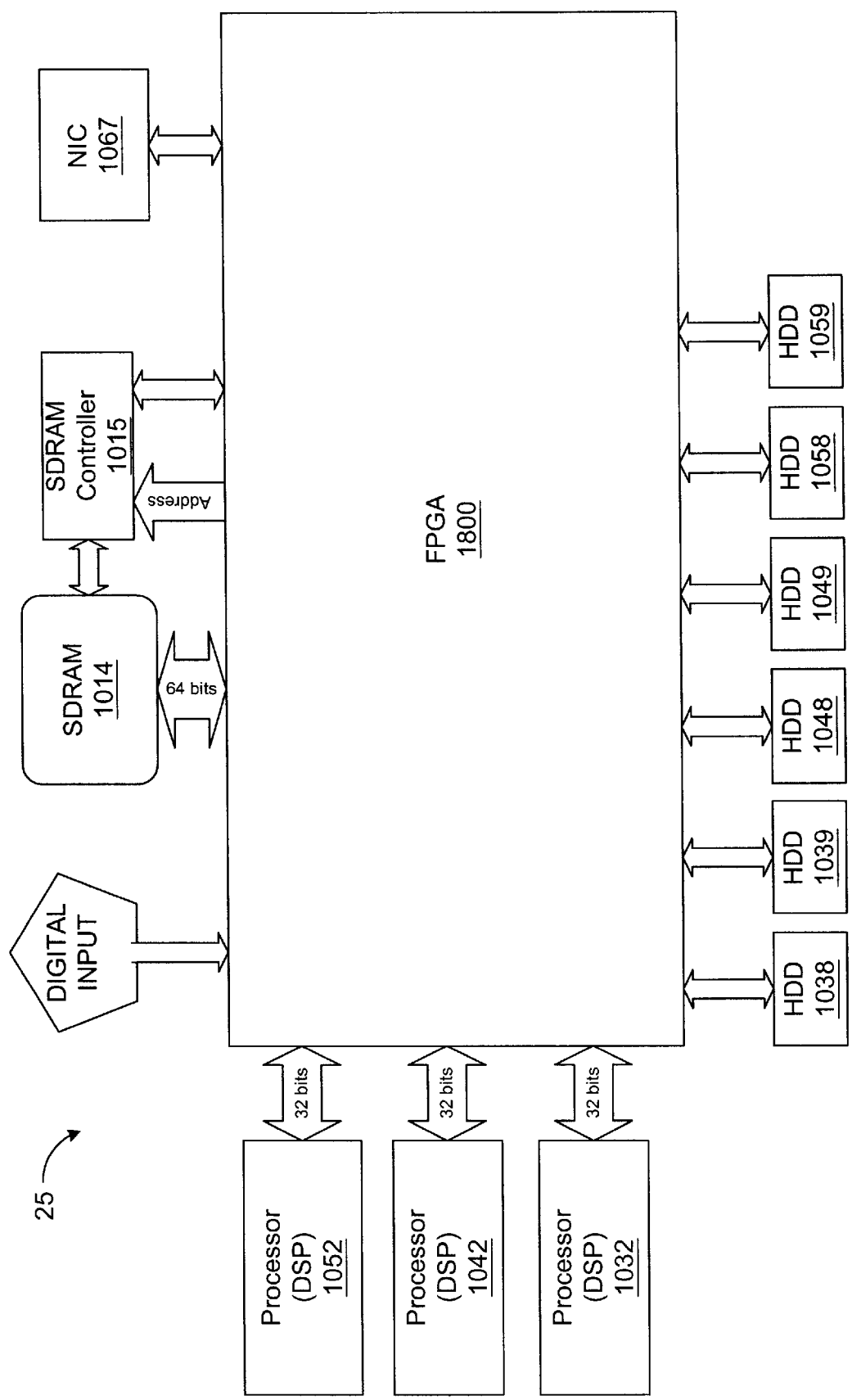

It is certified that error appears in the above-identified patent and that said Letters Patent is hereby corrected as shown below:

Drawings,
Delete all drawings (Fig. 1 - Fig. 14).

Signed and Sealed this

Thirteenth Day of July, 2004

JON W. DUDAS
*Acting Director of the United States Patent and Trademark Office*